United States Patent [19]

Mori et al.

[11] Patent Number: 5,227,541
[45] Date of Patent: Jul. 13, 1993

[54] PURIFICATION OF 2,3-DICHLORO-1-PROPANOL

[75] Inventors: Toshio Mori; Hiromitu Nojima; Koji Kudo, all of Kanagawa; Tatsuharu Arai, Tokyo, all of Japan

[73] Assignee: Showa Denko K.K., Tokyo, Japan

[21] Appl. No.: 982,119

[22] Filed: Nov. 25, 1992

Related U.S. Application Data

[63] Continuation of Ser. No. 814,467, Dec. 30, 1991, abandoned.

[51] Int. Cl.$^5$ .............................................. C07C 31/34
[52] U.S. Cl. ...................................... 568/850; 568/913
[58] Field of Search ...................... 568/848, 913, 850; 203/39, 81

[56] References Cited

U.S. PATENT DOCUMENTS 3,891,511  6/1975  Danneil et al. ..................... 203/81
4,634,784  1/1987  Nagato et al. .

Primary Examiner—Marianne M. Cintins
Assistant Examiner—Rebecca Cook
Attorney, Agent, or Firm—Sughrue, Mion, Zinn, Macpeak & Seas

[57] ABSTRACT

A process for purifying 2,3-dichloro-1-propanol is disclosed, which comprises introducing a chlorination reaction mixture obtained by chlorination of allyl alcohol in a hydrochloric acid aqueous solution in a reactor, to a degassing tower, where hydrogen chloride is released, returning the hydrogen chloride to the chlorination reactor, cooling the residual liquid to separate into an aqueous layer and an oily layer, and returning the aqueous layer to the chlorination reactor while recovering 2,3-dichloro-1-propanol from the oily layer, wherein said oily layer is introduced to a first distillation tower, where hydrogen chloride, part of the produced 2,3-dichloro-1-propanol, and other low-boiling components are recovered as a distillate, cooling the distillate to separate it into an aqueous layer and an oily layer, returning the aqueous layer of the distillate to the chlorination reactor, and recovering 2,3-dichloro-1-propanol from the oily layer of the distillate and a high-boiling fraction of the first distillation tower. Where 2,3-dichloro-1-propanol is for use as a starting material of epichlorohydrin, the process involves no wasteful consumption of calcium hydroxide.

3 Claims, 2 Drawing Sheets

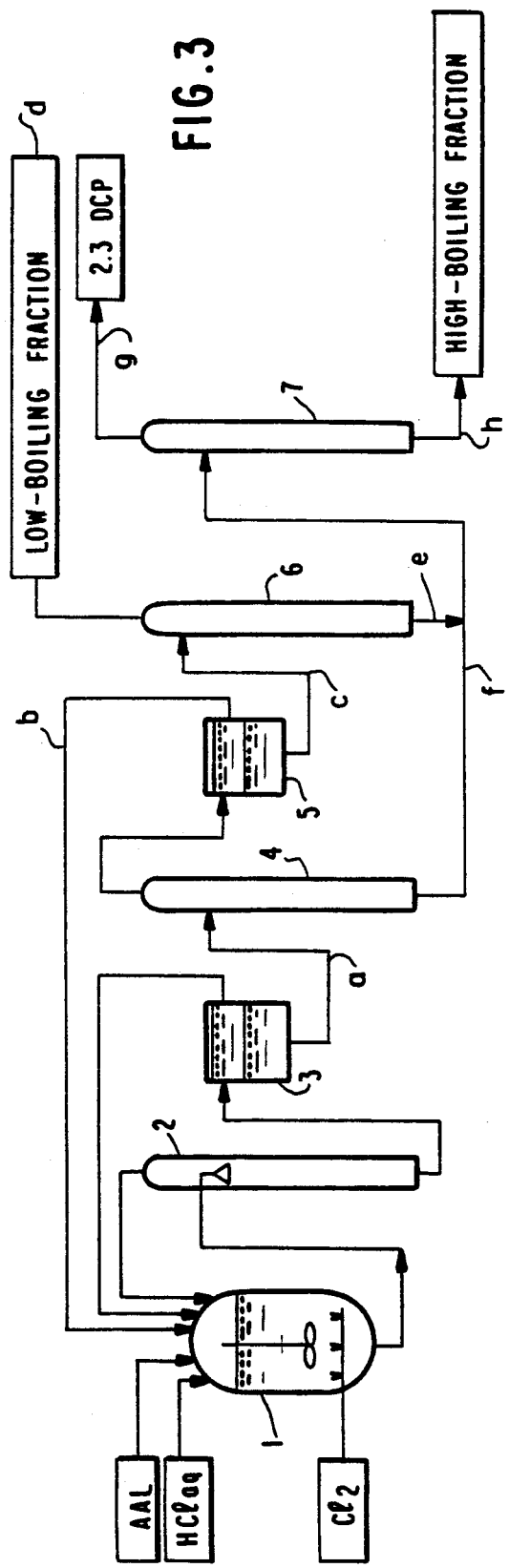
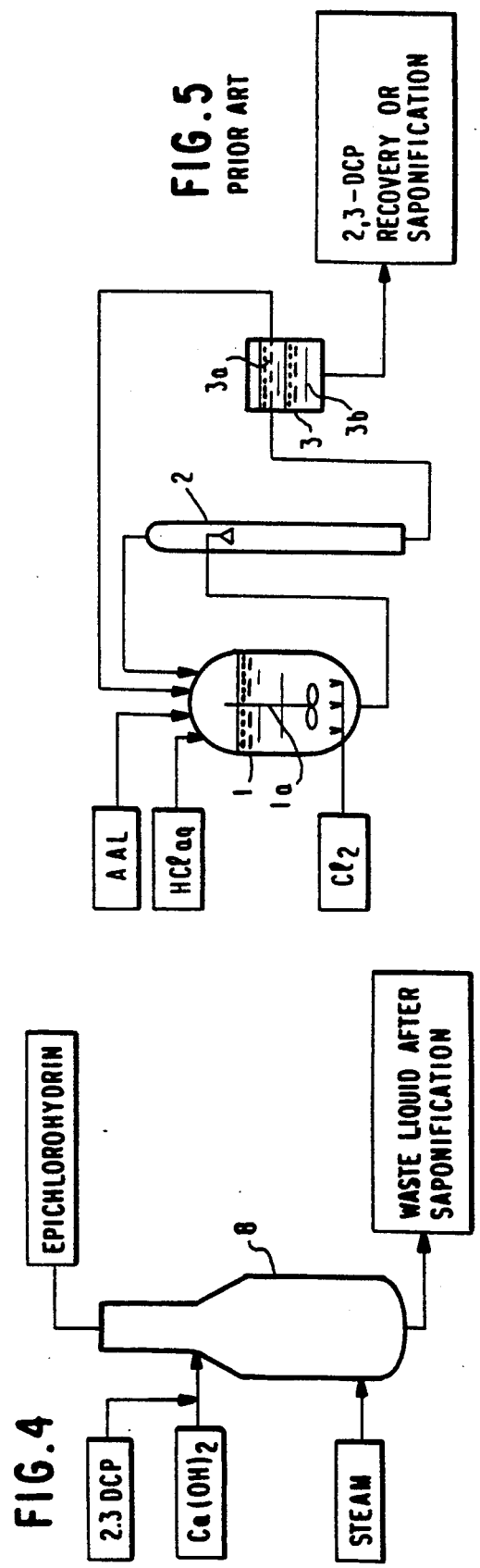

PURIFICATION OF 2,3-DICHLORO-1-PROPANOL

This is a continuation of application Ser. No. 07/814,467 filed Dec. 30, 1991 abandoned.

FIELD OF THE INVENTION

This invention relates to a process for purifying 2,3-dichloro-1-propanol (hereinafter abbreviated as 2,3-DCP). More particularly, it relates to an efficient process for purifying 2,3-DCP prepared by chlorination of allyl alcohol with chlorine in hydrochloric acid.

BACKGROUND OF THE INVENTION 2,3-DCP is used in quantities as an intermediate for synthesizing epichlorohydrin useful as a solvent, a starting material for epoxy resins, a starting material for synthetic rubber, a stabilizer for chlorinated rubber, etc.

Conventional production and purification of 2,3-DCP is illustrated in the system diagram of FIG. 5. In FIG. 5, a hydrochloric acid aqueous solution (HClaq) and allyl alcohol (AAL) are charged in reactor 1 equipped with stirrer 1a, and chlorine gas is blown through the AAL solution in the HClaq while cooling the solution at a constant temperature to produce 2,3-DCP. The reaction mixture is forwarded to degassing tower 2, where hydrogen chloride is evolved and returned to reactor 1. The degassed mixture is then delivered to first decanter 3, where it is separated into aqueous layer 3a and oily layer 3b by cooling to 40° C. or lower. Aqueous layer 3a is recycled to reactor 1, while oily layer 3b is recovered for direct use as a raw material for other compounds or purified to recover 2,3-DCP therefrom. For the conventional production of 2,3-DCP, reference can be made to U.S. Pat. No. 4,634,784.

Oily layer 3b comprises 72 to 75% by weight of 2,3-DCP, 3 to 6% by weight of by-products, e.g., glycerin monochlorohydrin and oligomers, and about 20% by weight of HClaq as an azeotropic component (20%).

For the production of epichlorohydrin, 2,3-DCP is once recovered from oily layer 3b and saponified by reaction with a calcium hydroxide aqueous solution, or oily layer 3b as separated in decanter 3 is directly subjected to saponification.

The former process in which the oily layer is purified involves an extra cost for separation into components and treatment of unnecessary and harmful components.

The latter process in which the oily layer is saponified as such is economically disadvantageous in that useful by-products such as glycerin monochlorohydrin cannot be recovered because they are incorporated into the waste liquor of the saponification mixture. Further, the hydrochloric acid contained in the oily layer is concurrently neutralized with calcium hydroxide, leading to not only wasteful consumption of calcium hydroxide but also necessity of making up for the loss of hydrochloric acid which is withdrawn from the chlorination system and is never recovered.

SUMMARY OF THE INVENTION

An object of the present invention is to provide a process for purifying 2,3-DCP which involves no wasteful consumption of calcium hydroxide when 2,3-DCP is for use as a starting material of epichlorohydrin, which allows, if desired, recovery of by-products, and which reduces the amount of a hydrochloric acid aqueous solution to be supplied to a chlorination reactor.

The present invention relates to a process for purifying 2,3-DCP, which comprises introducing a chlorination reaction mixture obtained by chlorination of allyl alcohol in a hydrochloric acid aqueous solution in a chlorination reactor, to a degassing tower, where hydrogen chloride is released, returning the hydrogen chloride to the chlorination reactor, cooling the residual liquid to separate into an aqueous layer and an oily layer, and returning the aqueous layer to the chlorination reactor while recovering 2,3-DCP from the oily layer, wherein said oily layer is introduced to a first distillation tower, where hydrogen chloride, part of the produced 2,3-DCP and other low-boiling components having a boiling point not higher than the boiling point of 2,3-DCP are recovered as a distillate, cooling the distillate to separate it into an aqueous layer and an oily layer, returning the aqueous layer of the distillate to the chlorination reactor, and recovering 2,3-DCP from the oily layer of the distillate and a high-boiling fraction of the first distillation tower having a boiling point not lower than the boiling point of 2,3-DCP.

If necessary, the oily layer separated from the distillate of the first distillation tower is further introduced to a second distillation tower, where a low-boiling fraction having a lower boiling point than the boiling point of 2,3-DCP is separated while recovering 2,3-DCP from a high-boiling fraction (bottom residue) having a boiling point not lower than the boiling point of 2,3-DCP, which mainly comprises 2,3-DCP and the high-boiling fraction of the first distillation tower.

If further necessary, the high-boiling fraction of the first and second distillation tower may be introduced to a third distillation tower, where 2,3-DCP is recovered as a distillate.

BRIEF DESCRIPTION OF THE DRAWINGS

FIGS. 1 through 3 are system diagrams each illustrating an embodiment of the process according to the present invention.

FIG. 4 shows a saponification tower.

FIG. 5 is the system diagram of a conventional process.

DETAILED DESCRIPTION OF THE INVENTION

The present invention is explained by referring to FIGS. 1 to 4 illustrating the flow of the process according to the present invention.

Figure 1:
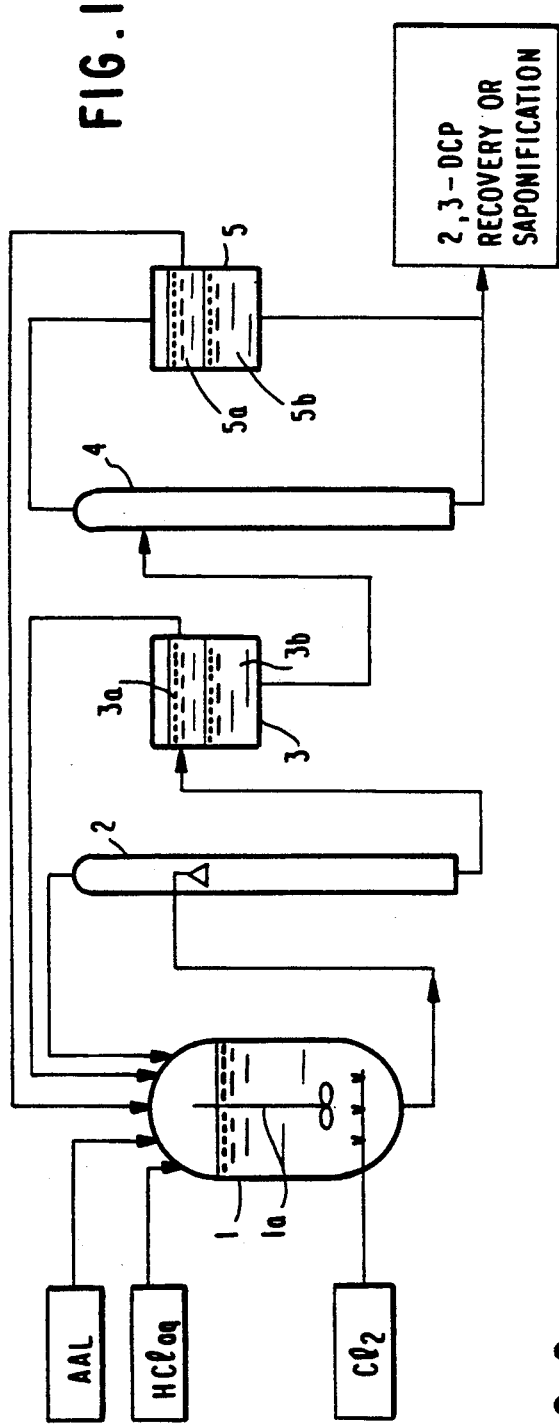

In FIG. 1, first distillation tower 4 is provided, into which the oily layer in first decanter 3 is introduced. The low-boiling fraction having a boiling point not higher than that of 2,3-DCP is forwarded to second decanter 5 where it is separated into aqueous layer 5a and oily layer 5b. Aqueous layer 5a is returned to reactor 1, while oily layer 5b and the high-boiling fraction of first distillation tower 4 are delivered to a step of 2,3-DCP recovery or saponification. In the first distillation, both the low- and high-boiling fractions contain large amounts of 2,3-DCP. The low-boiling fraction generally contains, other than 2,3-DCP (boiling point (b.p.) 182° C. at 1 atm), trichloropropane (b.p. 156.8° C. at 1 atm) and other low-boiling components such as an azeotropic mixture of hydrochloride and water (weight ratio 1:4; b.p. 110° C. at 1 atm), and the high-boiling fraction generally contains 2,3-DCP and glycerine monochlorohydrin (b.p. 213° C. at 1 atm). The first distillation is preferably carried out at the bottom temperature of 110° to 140° C. under atmospheric pressure.

Through the above-described flow of operation, the amount of a hydrochloric acid aqueous solution in the liquid fed to the step of 2,3-DCP recovery or saponification is greatly reduced. That is, the requisite amount of a hydrochloric acid aqueous solution to be supplied to reactor 1 is minimized. Where the oily layer 5b and the high-boiling fraction of first distillation tower 4 are fed to a saponification step, waste of calcium hydroxide can be reduced.

Figure 2:
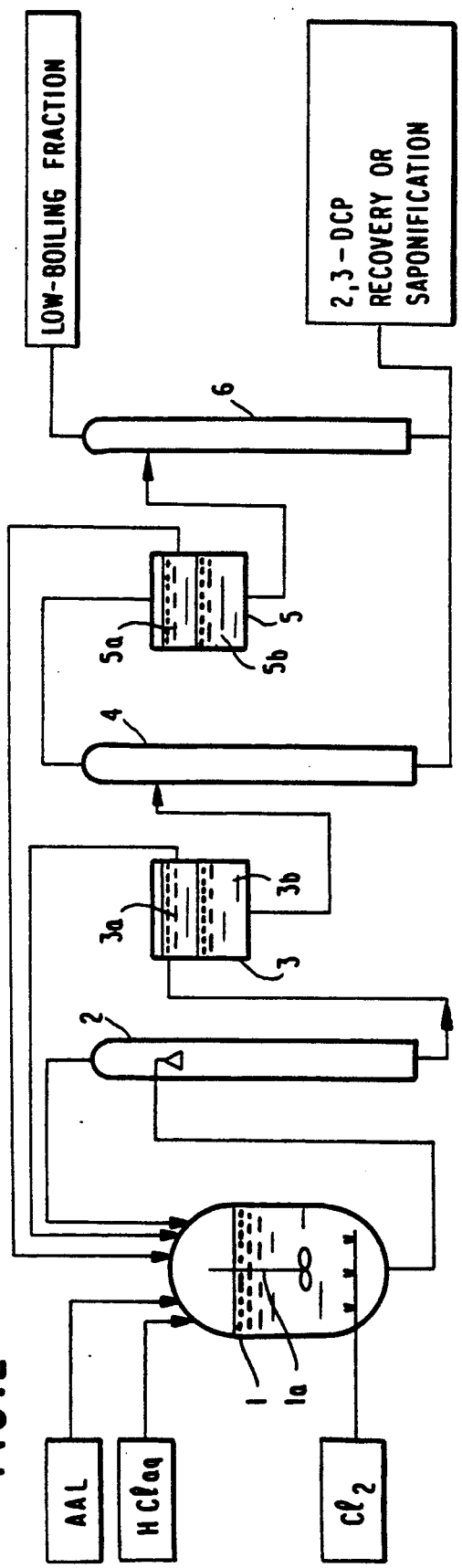

FIG. 2 illustrates a flow having second distillation tower 6 in addition to the first distillation tower of FIG. 1. Oily layer 5b of second decanter 5 is introduced to second distillation tower 6, where a low-boiling fraction having a boiling point lower than that of 2,3-DCP is removed. The high-boiling fraction from first distillation tower 4 and that from second distillation tower 6 are forwarded to a step of 2,3-DCP recovery or saponification. The high-boiling fractions of first and second distillation towers 4, 6 contain substantially no hydrochloric acid, waste of calcium hydroxide in the saponification step can be avoided. Further, the low-boiling fraction of second distillation tower 6 contains substantially no hydrochloric acid, low-boiling components which may be made use of can be recovered from this fraction. Almost all of hydrochloric acid withdrawn from reactor 1, other than that discharged as a low-boiling fraction from distillation tower 6, can be returned to reactor 1. Accordingly, the amount of a hydrochloric acid aqueous solution that should be supplied to reactor 1 is only the amount corresponding to the loss of the hydrochloric acid discharged as a low-boiling fraction. The second distillation is preferably carried out at the bottom temperature of 110° to 140° C. under a pressure of 100 to 200 mmHg ab.

FIG. 3 illustrates a flow having third distillation tower 7 in addition to the second distillation tower of FIG. 2. The high-boiling fractions from the first and second distillation towers are introduced to third distillation tower 7. Since these fractions delivered to third distillation tower 7 contains substantially no low-boiling substance having a boiling point lower than that of 2,3-DCP, 2,3-DCP is distilled off from the top of third distillation tower 7 while withdrawing a high-boiling fraction having a boiling point higher than that of 2,3-DCP as a bottom residue. The third distillation is preferably carried out at the bottom temperature of 110° to 140° C. under a pressure of 10 to 100 mmHg ab.

Through the above described flow of operation, the high-boiling fraction, the low-boiling fraction, and purified 2,3-DCP can be recovered individually. If desired, the low-boiling and high-boiling fractions separately recovered may be purified to obtain useful components, such as glycerin monochlorohydrin. Alternatively, the low-boiling and high-boiling fractions comprising organic chlorinated substances may be used as fuels for steam generation, or they may be burnt to recover hydrogen chloride as a by-product.

Using the thus recovered 2,3-DCP as a starting material, epichlorohydrin can be synthesized with good efficiency by a conventional saponification step as described in U.S. Pat. No. 4,634,784. For example, 2,3-DCP or an aqueous solution thereof is mixed with calcium hydroxide in a liquid phase, and the mixture is fed to saponification tower 8 while steam is fed from the bottom of the tower as illustrated in FIG. 4. An azeotropic mixture of the resultant epichlorohydrin and water is boiled at a boiling point of 88° C. Thus, the desired epichlorohydrin is stripped.

According to the present invention, the content of the hydrochloric acid aqueous solution in the liquid fed to a saponification step, etc. is markedly decreased so that waste of calcium hydroxide can be avoided in the saponification step. Moreover, the low- and high-boiling fractions may further be separated into constituting components, and highly concentrated 2,3-DCP can be used as a raw material of saponification.

The present invention is now illustrated in greater detail by way of Example, but it should be understood that the present invention is not deemed to be limited thereto.

EXAMPLE 2,3-DCP was produced by use of the apparatus shown in FIG. 3 under the conditions shown below.

|  | Bottom Temperature (°C.) | Pressure mmHg ab |
|---|---|---|
| First Distillation | 120.5 | 800 |
| Second Distillation | 125.0 | 150 |
| Third Distillation | 130.5 | 40 |

The composition of the liquid or fraction at the position indicated by symbols (a) through (h) is shown in Table 1 below.

TABLE 1

| | Flow Rate (kg/hr) | Composition (wt %) | | | | |
|---|---|---|---|---|---|---|
| Position | | 2,3-DCP | Low-Boiling Fraction | High-Boiling Fraction | HCl | H$_2$O |
| (a) | 400 | 74.0 | 1.9 | 3.5 | 4.4 | 16.2 |
| (b) | 84 | 11.2 | 1.4 | — | 17.4 | 69.9 |
| (c) | 14 | 29.0 | 41.0 | — | 14 | 16.0 |
| (d) | 10 | 4.0 | 55.0 | — | 20.0 | 25.0 |
| (e) | 4 | 86.0 | 14.0 | — | — | — |
| (f) | 302 | 93.5 | 0.2 | 4.6 | 0.3 | 1.3 |
| (g) | 289 | 97.6 | 0.2 | 0.5 | 0.3 | 1.3 |
| (h) | 13 | 4.0 | — | 96.0 | — | — |

As described above, the 2,3-DCP purification process according to the present invention makes it possible to greatly reduce the requisite amount of a hydrochloric acid aqueous solution to be supplied to a reactor of chlorination. When the resulting 2,3-DCP is used as a raw material of epichlorohydrin, the unit of calcium hydroxide for production of epichlorohydrin can be reduced. Further, since 2,3-DCP, a high-boiling fraction, and a low-boiling fraction can be separately recovered, the purification process of the invention is advantageous for obtaining raw materials of not only saponification but of other reactions. If desired, useful by-products can be recovered. When any treatment for rendering by-products harmless is needed, such a treatment can be carried out with ease because the by-products are discharged as a low-boiling or high-boiling fraction.

While the invention has been described in detail and with reference to specific examples thereof, it will be apparent to one skilled in the art that various changes and modifications can be made therein without departing from the spirit and scope thereof.

What is claimed is:

1. A process for purifying 2,3-dichloro-1-propanol comprising the steps of:
   (1) chlorinating alcohol in a hydrochloric acid aqueous solution in a reactor to produce a reaction mixture containing 2,3-dichloro-1-propanol;

(2) introducing said reaction mixture containing 2,3-dichloro-1-propanol into a degassing tower, where hydrogen chloride is released, and returning the resulting released hydrogen chloride to the reactor;

(3) cooling the residual liquid obtained from step (2) so as to separate it into
  (i) a first aqueous layer, and
  (ii) a first oily layer;

(4) returning the first aqueous layer to the reactor;

(5) feeding said first oily layer to a first distillation tower, and separating said first oily layer into
  (i) a high boiling fraction containing purified 2,3-dichloro-1-propanol, wherein said high boiling fraction has a boiling point not lower than that of 2,3-dichloro-1-propanol, and
  (ii) a low boiling fraction containing hydrogen chloride, 2,3-dichloro-1-propanol and low boiling components having a boiling point lower than that of 2,3-dichloro-1-propanol, wherein the low boiling fraction is recovered as a distillate, and recovering said high boiling fraction containing purified 2,3-dichloro-1-propanol, (6) cooling the resulting distillate of step (5) so as to separate it into
  (i) a second aqueous layer, and
  (ii) a second oily layer containing purified 2,3-dichloro-1-propanol;

(7) returning the second aqueous layer to said reactor; and (8) recovering the second oily layer containing purified 2,3-dichloro-1-propanol.

2. The process of claim 1, wherein said second oily layer is introduced to a second distillation tower, and separated into
  (i) a low boiling fraction having a lower boiling point than that of 2,3-dichloro-1-propanol, and
  (ii) a high boiling fraction containing purified 2,3-dichloro-1-propanol, wherein said high boiling fraction has a boiling point not lower than that of 2,3-dichloro-1-propanol, and recovering said high boiling fraction of the second distillation tower containing purified 2,3-dichloro-1-propanol.

3. The process of claim 2, wherein said high-boiling fraction of the first distillation tower and said high boiling fraction from the second distillation tower are introduced to a third distillation tower, wherein 2,3-dichloro-1-propanol is recovered as a distillate.

* * * * *